United States Patent [19]

Michell

[11] Patent Number: 4,826,327
[45] Date of Patent: May 2, 1989

[54] DEWPOINT METER

[75] Inventor: Andrew K. Michell, Cambridge, England

[73] Assignee: Michell Instruments Ltd, Cambridge, England

[21] Appl. No.: 145,604

[22] Filed: Jan. 19, 1988

[30] Foreign Application Priority Data

Jan. 26, 1987 [GB] United Kingdom ............... 8701616

[51] Int. Cl.[4] ............................................. G01N 25/02
[52] U.S. Cl. .................................... 374/20; 73/336.5
[58] Field of Search ..................... 374/20, 19, 18, 17; 73/336.5, 29

[56] References Cited

U.S. PATENT DOCUMENTS 3,112,648 12/1963 Dulk et al. ........................ 73/336.5
3,319,457 5/1967 Leone .................................. 374/20
4,629,333 12/1986 Dosoretz et al. .................... 374/20

FOREIGN PATENT DOCUMENTS 2067292 7/1981 United Kingdom ............... 374/20

Primary Examiner—Stewart J. Levy
Assistant Examiner—Joseph W. Roskos
Attorney, Agent, or Firm—Jeffers, Hoffman & Niewyk

[57] ABSTRACT

A dewpoint meter has a sensor comprising a mirror (1) situated in a chamber (2) through which gas, the dewpoint of which is to be measured is passed through an inlet port (3) and an outlet port (4). The mirror (1) is cooled by a Peltier effect heat pump (11) and the formation of condensation on the mirror as it is cooled is detected by a detector comprising a light emitting diode (7) and a photodiode (8). The temperature at which condensation occurs, which is the dewpoint of the gas, is measured by a thermometer. Instead of transferring the heat from the heat pump (11) directly to a heat sink (13) as is usual, a heat pipe (12) is interposed between the heat pump (11) and the heat sink (13). This avoids the necessity for having the heat sink closely adjacent the mirror and thus avoids errors caused by heat from the heat sink affecting the temperature of the mirror.

6 Claims, 3 Drawing Sheets

4,826,327

DEWPOINT METER

BACKGROUND OF THE INVENTION

This invention relates to dewpoint meters, for measuring the dewpoint of a gas, of the kind which includes a sensor having a mirror or other surface exposed to the gas, an optical detector or other means which produces an electric signal upon the detection of condensation on the surface, an electrically operated device for controlling the temperature of the surface, the electrically operated device being controlled in dependence upon the signals produced by the detector or other means to maintain the temperature of the surface at that at which condensation just takes place upon it, and a thermometer to indicate the temperature of the surface at which condensation occurs, this being the dewpoint of the gas. Such a dewpoint meter is disclosed, for example, in U.S. Pat. No. 3,112,648.

SUMMARY OF THE INVENTION

According to this invention, a dewpoint meter of the kind just described is characterised by, a heat pipe between the surface and a heat sink for transferring excess heat from the surface, when its temperature is reduced, to the heat sink.

Some heat pipes have internal wicks and some do not. The latter are sometimes referred to as thermo-syphons. The term "heat pipe" in this specification is intended to cover heat pipes with and without internal wicks.

The invention is broadly applicable to dewpoint meters for two different purposes. The first is for measuring very high dewpoints of very hot gas streams, for example the gases in flue stacks. In dewpoint meters for this purpose, the surface may be heated by a resistive electrical heater and the heat pipe is then thermally connected directly to the surface and transfers heat from the surface to the ambient surroundings remote from the hot gas stream. In the case of flue gases in a stack, the heat pipe extends through the stack into the atmosphere, which forms the heat sink, outside the stack. The heat pipe transfers heat away from the surface at a rate greater than the surface gains heat from the gas stream and in consequence tends to cause the surface to fall to a temperature below the dewpoint of the gas. The resistive electric heater then heats the surface further to raise it to the dewpoint and is switched on and off under the control of the optical detector or other detecting means to maintain the temperature of the mirror at the dewpoint.

The second purpose is for measuring the dewpoint of the atmosphere or measuring the dewpoint of a gas at a temperature near or below that of the surrounding atmosphere. For this purpose, it is necessary to cool the mirror or other surface and to do this the electrically operated device is preferably a thermo-electric heat pump, for example a Peltier effect heat pump. The heat pump may then be interposed between the surface and the heat pipe and it then transfers heat from the surface to one end of the heat pipe, the other end of which is in thermal contact with the heat sink. As an alternative, the heat pump may be interposed between the heat pipe and the heat sink. In this case the heat pipe transfers heat from the surface to the heat pump and the heat pump passes the heat on to the heat sink.

In existing dewpoint meters of the kind initially described, it is conventional to provide a Peltier effect heat pump to transfer heat from the surface to a heat sink, but this has always taken place directly so that the heat sink is closely adjacent to the surface.

One disadvantage of this conventional arrangement is that the heat discharged by the heat pump may be quite high and to dispose of it, a large heat sink is necessary. This is cumbersome and it is difficult to incorporate the heat sink within the sensor. What is more, the close proximity of the heat sink to the surface causes heat from the sink to affect the temperature of the surface and conversely the proximity of the surface to the heat sink affects the cooling performance of the heat sink.

By interposing a heat pipe between the mirror or other surface and the heat sink, it has been found that it is possible to use a smaller heat sink and also, of course, the heat sink can be situated far enough away from the surface so that the heat sink and the surface have no adverse effects on each other.

Further, the provision of the heat pipe enables the surface to have its temperature reduced by the heat pump to a lower value than is possible with the conventional arrangement and in consequence the dewpoint meter has a wider operating range.

BRIEF DESCRIPTION OF THE DRAWINGS

Two examples of dewpoint meter in accordance with the invention will now be described with reference to the accompanying drawings, in which.

DESCRIPTION OF PREFERRED EXAMPLE

Figure 1:
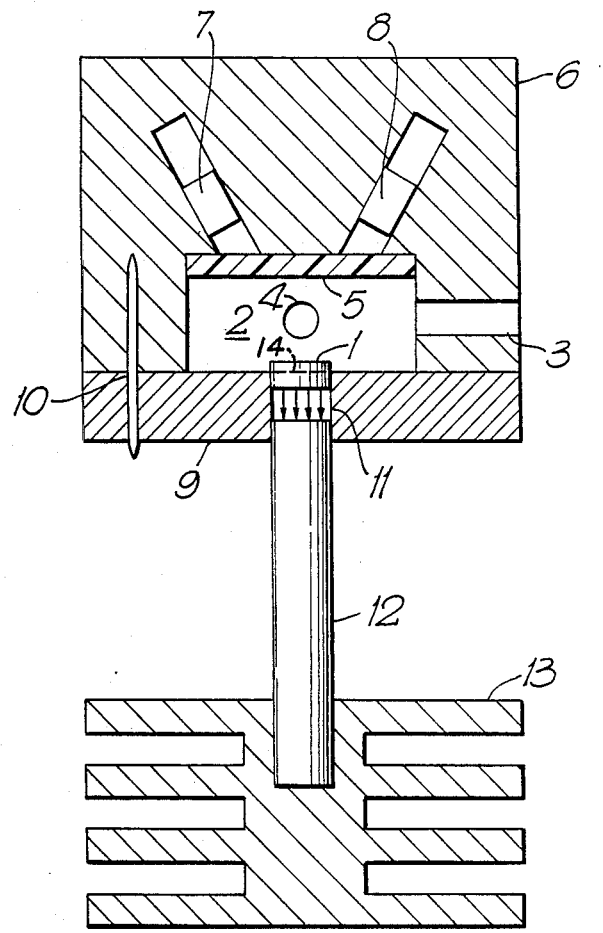
FIG. 1 is a diagrammatic side view, partly in section, of the sensor of the first example; and, FIG. 2 is a similar view of the second example.

Referring to FIG. 1, the sensor comprises a mirror 1 which incorporates a platinum resistance thermometer and is situated in a chamber 2. The chamber 2 has a gas inlet port 3 and a gas outlet port 4. The face of the chamber 2 remote from the mirror 1 is covered by a window 5 of glass or perspex and behind the window 5 within a block 6 are a light source in the form of a light emitting diode 7 and a light sensor in the form of a photo diode 8.

The mirror 1 is held within a cover 9, which is clamped to the block 6 with a pressure pad connection 10 interposed between them to connect the light emitting diode 7 and the photo diode 8 in their respective electrical circuits.

Also within the cover 9 in contact with the rear face of the mirror 1 is a Peltier effect heat pump or heater 11, the face of which remote from the mirror 1 is in contact with a heat pipe 12. The end of the heat pipe 12 remote from the heat pump or heater 11 is embedded in a finned copper, aluminium or brass block 13 which forms a heat sink.

As is usual with dewpoint meters of the kind initially described, light from the light emitting diode 7 is reflected from the mirror 1 to the photo diode 8 which produces a signal. The mirror 1 is cooled by the heat pump 11 until vapour in the gas in the chamber 2 is condensed upon it. This reduces the transmission of light from the light emitting diode 7 to the photo diode 8 and the change in the signal from the photo diode 8 is amplified and controls the heat pump or heater 11 to reduce its cooling or heating effect and maintain the mirror 1 at the dewpoint temperature at which condensation just takes place upon it. This temperature is indicated by the platinum resistance thermometer 14.

Instead of the heat pump 11 transferring heat from the mirror 1 directly to a heat sink immediately adjacent the cover 9, the heat is transferred by the heat pipe 12, which may be of any required length to the remote heat sink 13.

Figure 2:
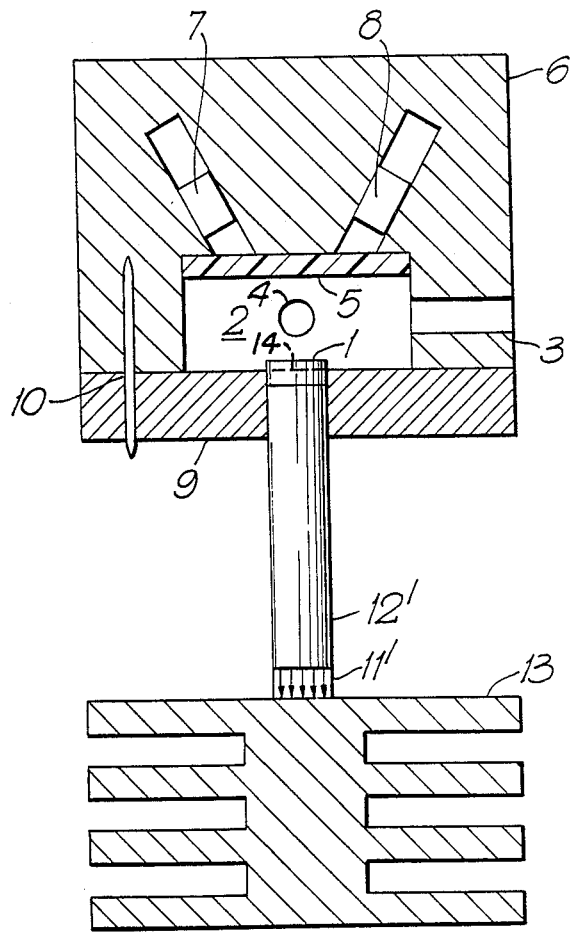

The second example shown in FIG. 2 is the same as the first example, and the same reference numerals are used for corresponding parts, with the exception that the heat pipe 12' is in direct contact with the mirror 1 and the heat pump 11' is interposed between the heat pipe 12' and the block 13, which forms the heat sink.

Figure 3:
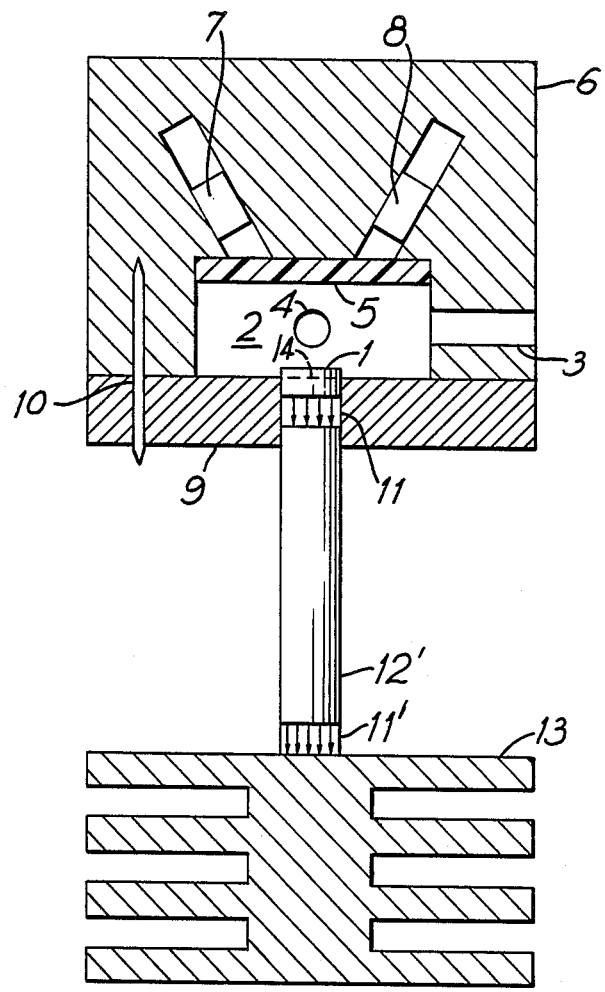
FIG. 3 is a similar view of the third example.

In a further modification shown in FIG. 3, two heat pumps 11 and 11' are provided, one between the mirror and the heat pipe 12' and the other between the heat pipe 12' and the heat sink 13.

I claim:

1. In a dewpoint meter for measuring the dewpoint of a gas, including a sensor comprising means defining a mirror-like surface for exposure to said gas, detector means for producing an electric signal upon detection of condensation on said surface, an electrically operated means for controlling the temperature of said surface in dependence upon said signal from said detector means to maintain the temperature of said surface at that at which condensation just takes place upon it and thermometer means to indicate the temperature of said surface at which said condensation occurs, the improvement comprising a heat sink for receiving excess heat from said surface when its temperature is reduced and a heat pipe between said surface and said heat sink for transmitting said excess heat from said surface to said heat sink.

2. A dewpoint meter as claimed in claim 1, for measuring high dewpoints of hot gas streams, wherein said electrically operated means is a resistive electrical heater for heating said surface, and further comprising means thermally connecting said heat pipe directly to said surface to transfer heat from said surface to ambient surroundings, which form said heat sink, remote from said hot gas stream.

3. A dewpoint meter as claimed in claim 1, for measuring the dewpoint of the atmosphere or a gas at a temperature near or below that of the atmosphere, wherein said electrically operated means is a thermoelectric heat pump which cools said surface.

4. A dewpoint meter as claimed in claim 3, in which said heat pump transfers heat from said surface to one end of said heat pipe, and further comprising means mounting the other end of said heat pipe in thermal contact with said heat sink.

5. A dewpoint meter as claimed in claim 3, further comprising means mounting one end of said heat pipe in thermal contact with said surface and wherein said heat pump transfers heat from the other end of said heat pipe to said heat sink.

6. A dewpoint meter as claimed in claim 1, in which said heat sink is a finned block made from a metal from a group consisting of copper, aluminium and brass.

* * * * *